(12) United States Patent
Liang et al.

(10) Patent No.: US 8,134,719 B2
(45) Date of Patent: Mar. 13, 2012

(54) 3-D IMAGING USING TELECENTRIC DEFOCUS

(75) Inventors: Rongguang Liang, Penfield, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 12/727,671

(22) Filed: Mar. 19, 2010

(65) Prior Publication Data
US 2011/0229840 A1    Sep. 22, 2011

(51) Int. Cl.
*G01B 11/14* (2006.01)
*G01B 11/00* (2006.01)

(52) U.S. Cl. ............. 356/625; 356/2; 356/624; 356/602

(58) Field of Classification Search .......... 356/600–604, 356/610, 612, 614, 623–625; 250/201.2, 250/201.4, 201.8; 433/215, 218, 223; 355/44, 355/40, 43
See application file for complete search history.

(56) References Cited

U.S. PATENT DOCUMENTS

| | | | |
|---|---|---|---|
| 5,135,308 A * | 8/1992 | Kuchel | 356/604 |
| 5,372,502 A * | 12/1994 | Massen et al. | 433/215 |
| 5,440,393 A | 8/1995 | Wenz | |
| 5,604,817 A * | 2/1997 | Massen et al. | 382/120 |
| 5,708,532 A | 1/1998 | Wartmann | |
| 6,000,939 A * | 12/1999 | Ray et al. | 433/27 |
| 6,068,482 A * | 5/2000 | Snow | 433/223 |
| 6,144,453 A | 11/2000 | Hallerman et al. | |
| 0,008,139 A1 | 1/2002 | Albertelli | |
| 6,424,404 B1 * | 7/2002 | Johnson | 355/44 |
| 6,573,998 B2 * | 6/2003 | Cohen-Sabban | 356/602 |
| 6,594,539 B1 | 7/2003 | Geng | |
| 6,603,103 B1 * | 8/2003 | Ulrich et al. | 250/205 |
| 6,697,164 B1 * | 2/2004 | Babayoff et al. | 356/609 |
| 6,870,609 B2 | 3/2005 | Watkins et al. | |
| 6,885,464 B1 | 4/2005 | Pfeiffer et al. | |
| 6,940,611 B2 | 9/2005 | Babayoff et al. | |
| 7,081,944 B2 * | 7/2006 | de Jager | 355/52 |

(Continued)

FOREIGN PATENT DOCUMENTS

WO    WO 98/29708    7/1998

OTHER PUBLICATIONS

"Telecentric Optics for Focus Analysis" in *IEEE Transactions on Pattern Analysis and Machine Intelligence*, vol. 19, No. 12, (1997) pp. 1360-1365. European Search Report, Application No. EP 11 00 2257, Sep. 6, 2011, 2 pages.

*Primary Examiner* — Sang Nguyen

(57) ABSTRACT

An apparatus for obtaining 3-D surface contour image data of a tooth has a double telecentric optical system disposed to form an image of the surface of the tooth onto an image detector array. A focus adjustment mechanism is actuable to adjust the position of either or both the double telecentric optical system and the image detector array along an optical axis to each of a sequence of focus positions. A control logic processor is in control signal communication with the focus adjustment mechanism to adjust focus position, and is in image data communication with the image detector array for receiving image data obtained by the image detector array and with a memory for storing the received image data corresponding to each of the sequence of focus positions. The control logic processor is further responsive to stored instructions for computing 3-D surface contour image data from the image data.

20 Claims, 16 Drawing Sheets

U.S. PATENT DOCUMENTS

| | | | |
|---|---|---|---|
| 7,342,668 B2 * | 3/2008 | Quadling et al. | 356/603 |
| 7,751,871 B2 * | 7/2010 | Rubbert | 600/476 |
| 7,929,151 B2 * | 4/2011 | Liang et al. | 356/601 |
| 2007/0086762 A1 | 4/2007 | O'Keefe et al. | |
| 2007/0165243 A1 | 7/2007 | Kang et al. | |
| 2008/0024768 A1 | 1/2008 | Babayoff | |
| 2009/0011386 A1 | 1/2009 | Eiff et al. | |

* cited by examiner

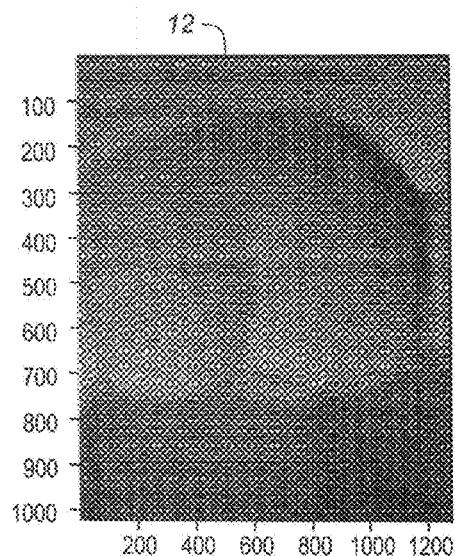 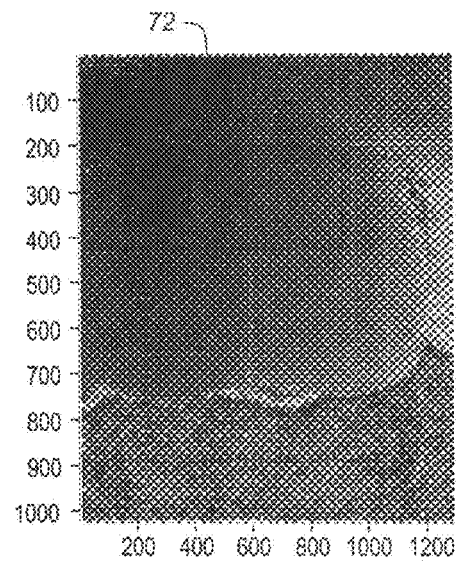
FIG. 13A    FIG. 13B
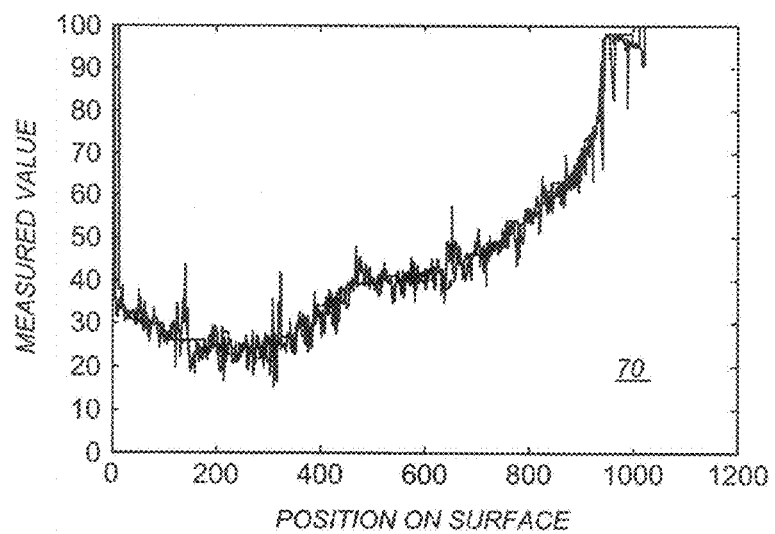
FIG. 13C

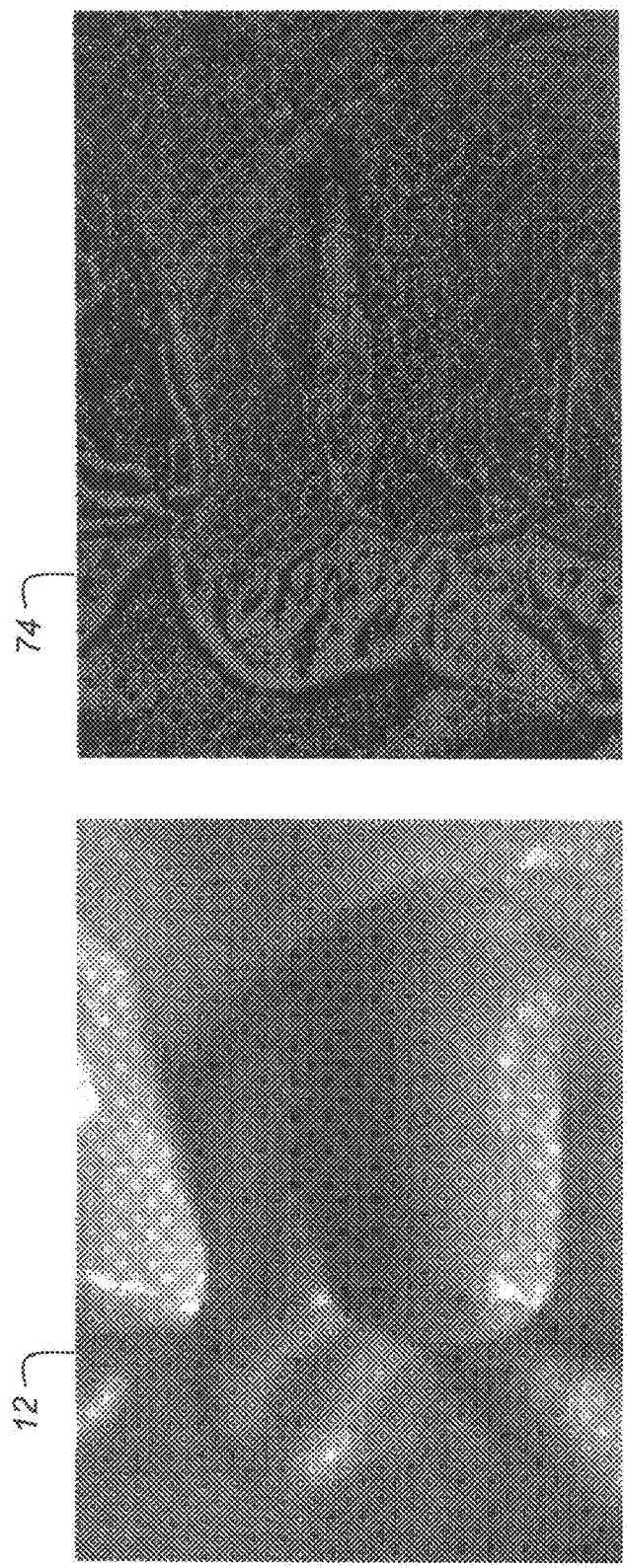

3-D IMAGING USING TELECENTRIC DEFOCUS

FIELD OF THE INVENTION

The invention relates generally to the field of diagnostic imaging and in particular to 3-D imaging of intra-oral surfaces. More specifically, the invention relates to apparatus and methods for 3-D imaging using telecentric optics in a focus-changing sequence.

BACKGROUND OF THE INVENTION

The capability for 3-D imaging of teeth and intra-oral structures in general can help to improve dental care and diagnosis and to provide more accurate data for preparation of dental appliances and prosthetics. Although there have been a number of proposed solutions to this problem, inherent difficulties with each of these approaches limit their usability, accuracy, and cost-effectiveness.

One conventional type of approach that has been proposed is contour or fringe projection imaging. Fringe projection imaging uses patterned or structured light to obtain surface contour information for complex structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. However, technical obstacles such as tooth translucency, light scattering, and high reflection levels complicate the surface reconstruction problem and limit effective use of fringe projection imaging of the tooth. Techniques to compensate for these problems, such as temporarily coating teeth surfaces to condition the tooth surface and enhance tooth opacity for example, add time and cost to the imaging process and can tend to mask other problems.

Other methods for intra-oral 3-D imaging include depth measurement using a hand-held optical probe, such as that described in U.S. Pat. No. 5,440,393 entitled "Process and Device for measuring the dimensions of a space, in particular a buccal cavity" to Wenz. Such devices, however, are limited to making very specific measurements and are not designed for 3-D imaging of the tooth surface for one or more teeth. Confocal imaging methods, such as taught, for example, in U.S. Pat. No. 6,697,164 entitled "Imaging a Three-Dimensional Structure by Confocal Focussing an Array of Light Beams" to Babayoff et al., illuminate a discrete number of spots on the tooth surface and use this sampling to map surface contour. However, a confocal approach of this type requires a relatively complex arrangement of illumination and sensing components. Moreover, the resulting surface contour information, once obtained, must then be correlated or registered to the tooth image itself in a separate processing operation.

Among the challenges faced by dental 3-D imaging systems are the highly pronounced contours of the tooth surface. It can be difficult to provide sufficient amounts of light onto, and sense light reflected back from, all of the tooth surfaces. The different surfaces of the tooth can be oriented at 90 degrees relative to each other, making it difficult to direct enough light for accurately imaging all parts of the tooth.

It can be appreciated that an apparatus and method that provides accurate surface contour imaging of the tooth, without the need for applying an added coating or other conditioning of the tooth surface for this purpose, would help to speed reconstructive dentistry and could help to lower the inherent costs and inconvenience of conventional methods for obtaining surface contour information, such as those for obtaining a cast or other surface profile for a crown, implant, or other restorative structure.

SUMMARY OF THE INVENTION

An object of the present invention is to obtain 3-D image data from the surface of a tooth or other intra-oral structure. A related object is to obtain this image data using a double telecentric optical system.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided an apparatus for obtaining 3-D surface contour image data of a tooth, the apparatus comprising: a focus adjustment mechanism that is actuable to adjust the position of either or both the double telecentric optical system and the image detector array along an optical axis to each of a sequence of focus positions; and a control logic processor that is in control signal communication with the focus adjustment mechanism to adjust focus position, and that is in image data communication with the image detector array for receiving image data obtained by the image detector array and with a memory for storing the received image data corresponding to each of the sequence of focus positions, wherein the control logic processor is further responsive to stored instructions for computing the 3-D surface contour image data from the stored image data.

According to another aspect of the invention, there is provided a method for obtaining 3-D surface contour image data of a tooth, the method comprising: disposing, in the image plane of a double telecentric optical system, an image detector array that is energizable to form an image; adjusting the position of either or both the double telecentric optical system and the image detector array along an optical axis to each of a sequence of focus positions; obtaining image data from the detector array at each focus position in the sequence and storing the image data in an electronic memory; calculating the focus of each of a plurality of pixels in the obtained image data and determining, for each of the pixels, a corresponding depth value according to pixel contrast; combining a plurality of the determined depth values to form the 3-D surface contour image; and displaying the 3-D surface contour image.

Advantageously, the obtained image data can be readily displayed along with the calculated surface contour data, since a pixellated image detector is used for obtaining the surface information.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other. Angular and spatial relationships may be represented in a compressed or exaggerated manner in order to illustrate principles or behavior that is of particular interest.

FIGS. 13A, 13B, and 13C show profile data and a portion of the surface reconstruction for a tooth using focus information according to one embodiment.

FIGS. 14A and 14B show a portion of the surface of an artificial tooth that is exceptionally smooth and presents a challenge for obtaining accurate surface data.

DETAILED DESCRIPTION OF THE INVENTION

Figure 1:
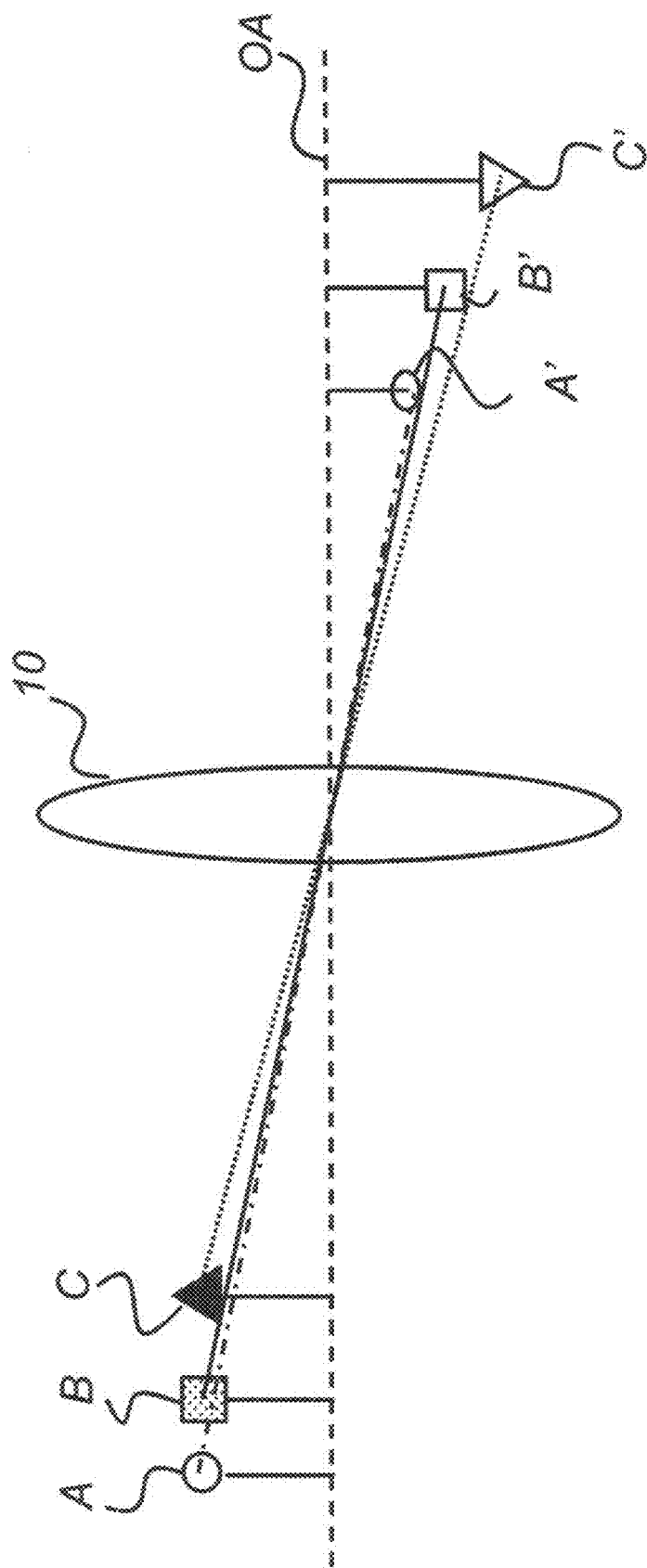
FIG. 1 is a schematic showing magnification effects of conventional non-telecentric optics.

The following is a detailed description of the preferred embodiments of the invention, reference being made to the drawings in which the same reference numerals identify the same elements of structure in each of the several figures.

The apparatus and methods of the present invention obtain 3-D depth information from images by using telecentric defocus. In order to more fully understand the principles and operation of the present invention, it is instructive to review telecentricity in general and, more specifically, to describe the operation of the double telecentric optics of the apparatus of the present invention.

The schematic diagram of FIG. 1 shows how a lens 10 forms an image in a conventional, non-telecentric imaging system. In the object space to the left of lens 10, objects A, B, and C are all the same height. In image space, however, images A', B', and C' are of different heights. Following this conventional model, the further the object is from the lens, the lower the effective magnification.

Figure 2:
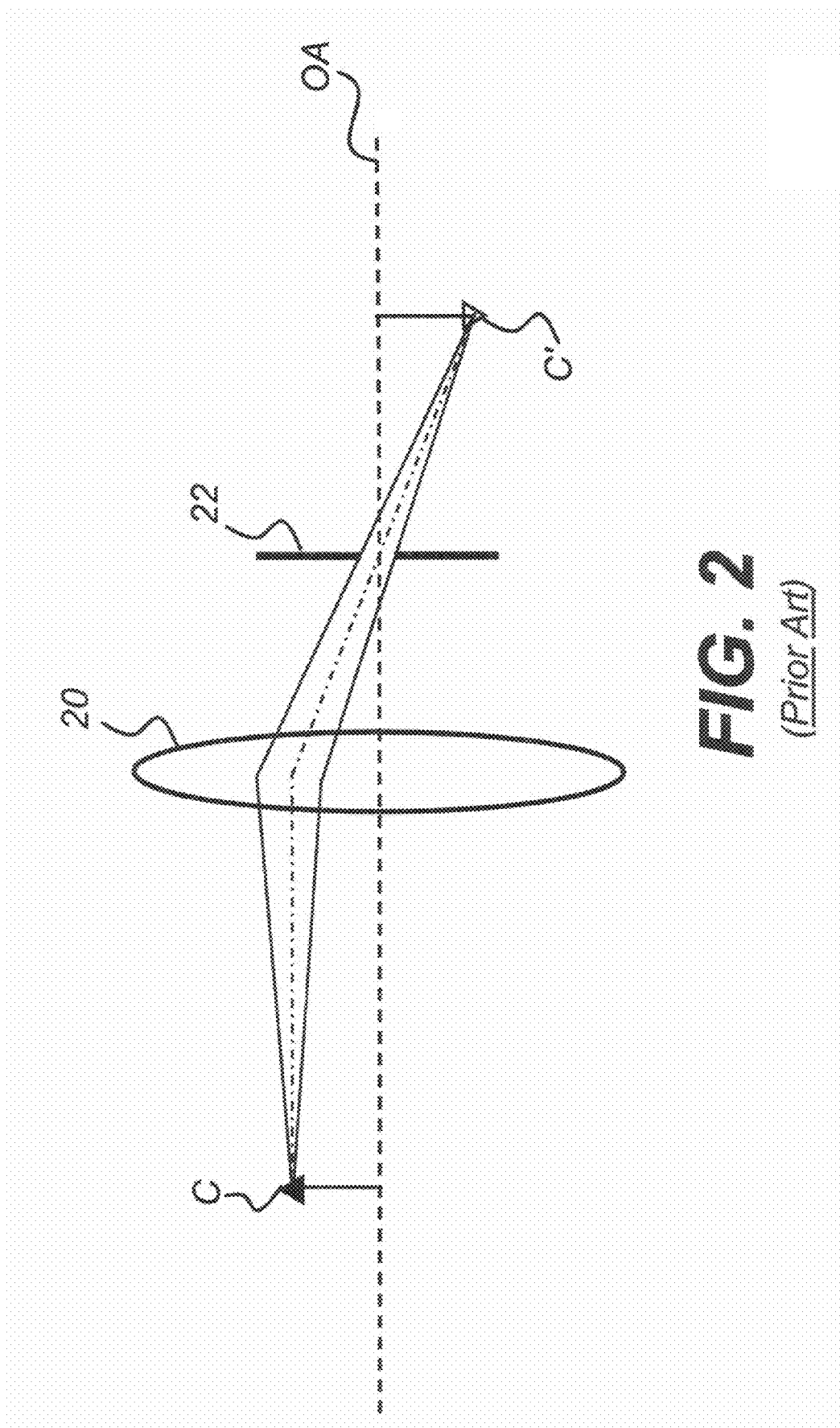
FIG. 2 is a schematic diagram showing the behavior of object-telecentric optics.

The schematic diagram of FIG. 2 shows principles of an object-space telecentric optical apparatus. Unlike the non-telecentric example of FIG. 1, the chief ray from the object field, shown (by a phantom line) as the central ray emanating from object C in FIG. 2, is parallel to the optical axis OA. A stop 22 limits the angular range of light rays from the object field. On the object side, the chief ray is parallel to the optical axis. Object-space telecentric optics require that lens 20 have a sufficiently large diameter for receiving light from the object field, with the basic geometry shown in FIG. 2. A number of object-space telecentric lenses are available for particular applications. However, due to the large field of view that is required, object-space telecentricity is not practical for many types of imaging systems.

Figure 3:
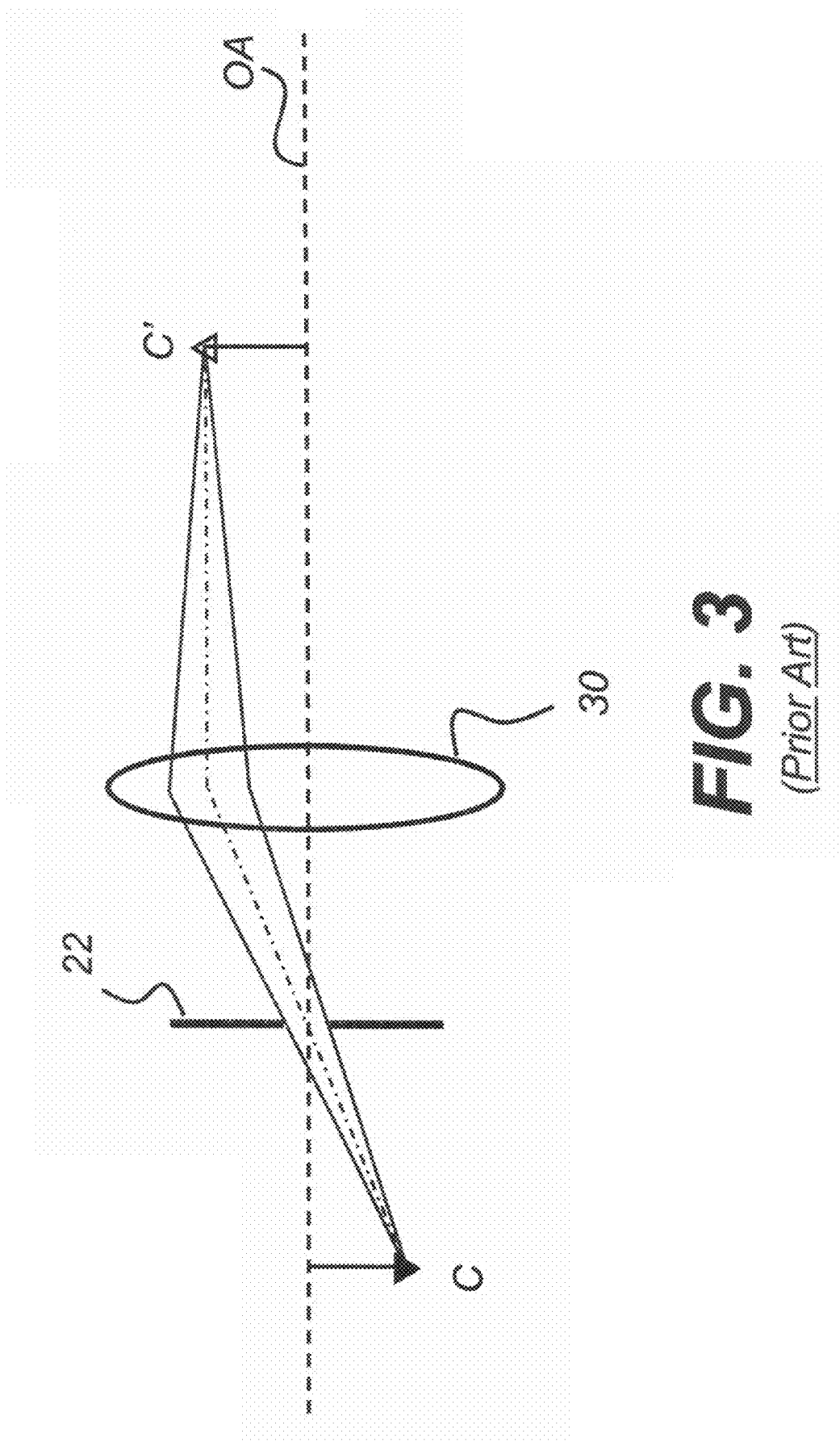
FIG. 3 is a schematic diagram showing the behavior of object-telecentric optics.

The schematic diagram of FIG. 3 shows an image-space telecentric optical apparatus. With this arrangement, the chief ray in the image field extends in parallel to the optical axis. Therefore, the magnification remains constant as the image position shifts along the optical axis, with changing focus. With constant magnification, there is no need to re-scale and register images for image processing. Recognizing this advantage for image telecentric optics, researchers Masahiro Watanabe and Shree K. Nayar in an article entitled "Telecentric Optics for Focus Analysis" in *IEEE Transactions on Pattern Analysis and Machine Intelligence*, vol 19 no. 12, (1997) p. 1360-5 describe an image-space telecentric system using commercially available machine-vision lenses. By using a suitable arrangement of apertures, Watanabe et al. describe how to transform off-the-shelf lenses for an image-space telecentric system that is used for range sensing based on determining depth from defocus.

The image system described in the Watanabe et al. article, which is telecentric only in image space, can be used to improve machine vision system performance, but has a number of shortcomings that make it less desirable for use in dental imaging applications. Shadowing can result from head-on imaging of a tooth or other object with relatively steep edges, for example. In addition, sensor pixels correspond to different object points as the sensor moves along the optical axis. Therefore, scaling adjustment is necessary in order to extract depth information when using image-space telecentric optics.

Embodiments of the present invention address the problem of depth detection for dental imaging applications also using telecentric optical design principles, but without the constraints and limitations described above. In order to more fully appreciate the operation and features of the present invention, it is first useful to review double telecentric imaging apparatus that provide both the object-side telecentricity previously described with reference to FIG. 2 and the image-side telecentricity taught by Watanabe et al. and previously described with reference to FIG. 3.

Figure 4:
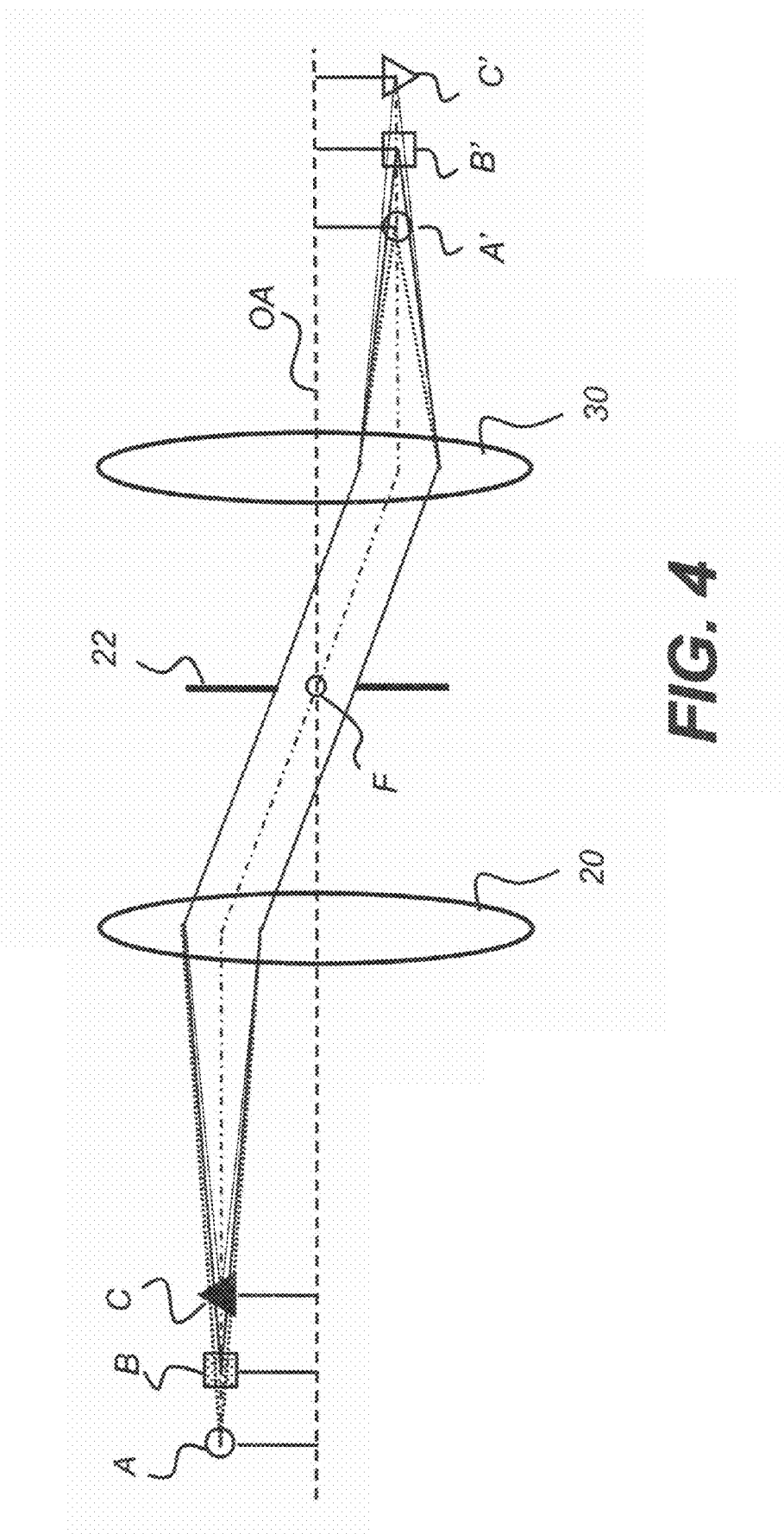
FIG. 4 is a schematic diagram showing the behavior of double telecentric optics.

A double telecentric imaging apparatus has the arrangement shown schematically in FIG. 4. Here, stop 22 is positioned at the common focal point F of lenses 20 and 30 so that the chief ray is parallel in both object and image space. In the image space, images A', B', and C' are of the same height for objects A, B, and C of the same height, as shown, regardless of their distance from lens 20.

A number of related observations can be made concerning the double telecentric optical arrangement shown in FIG. 4:

(i) Magnification is maintained. Regardless of focus adjustment, the magnification of each object in the object field remains the same. With varying focus, images blur symmetrically as focus changes.

(ii) The telecentric lens "views" the object field from the same perspective angle, at any focus position.

(iii) For any point on the object, the chief ray angle is zero or at least very low, typically within a fraction of a degree. Similarly, the chief ray angle in the image plane is also very low.

(iv) Objective lens 20 must still have sufficient diameter for receiving light from the object field, as noted for object-side telecentric systems. In practice, this means that the diameter of lens 20 should be larger than the dimension of the tooth surface that is to be imaged.

(v) Each pixel (image point) corresponds solely to only a single object point.

Figure 5:
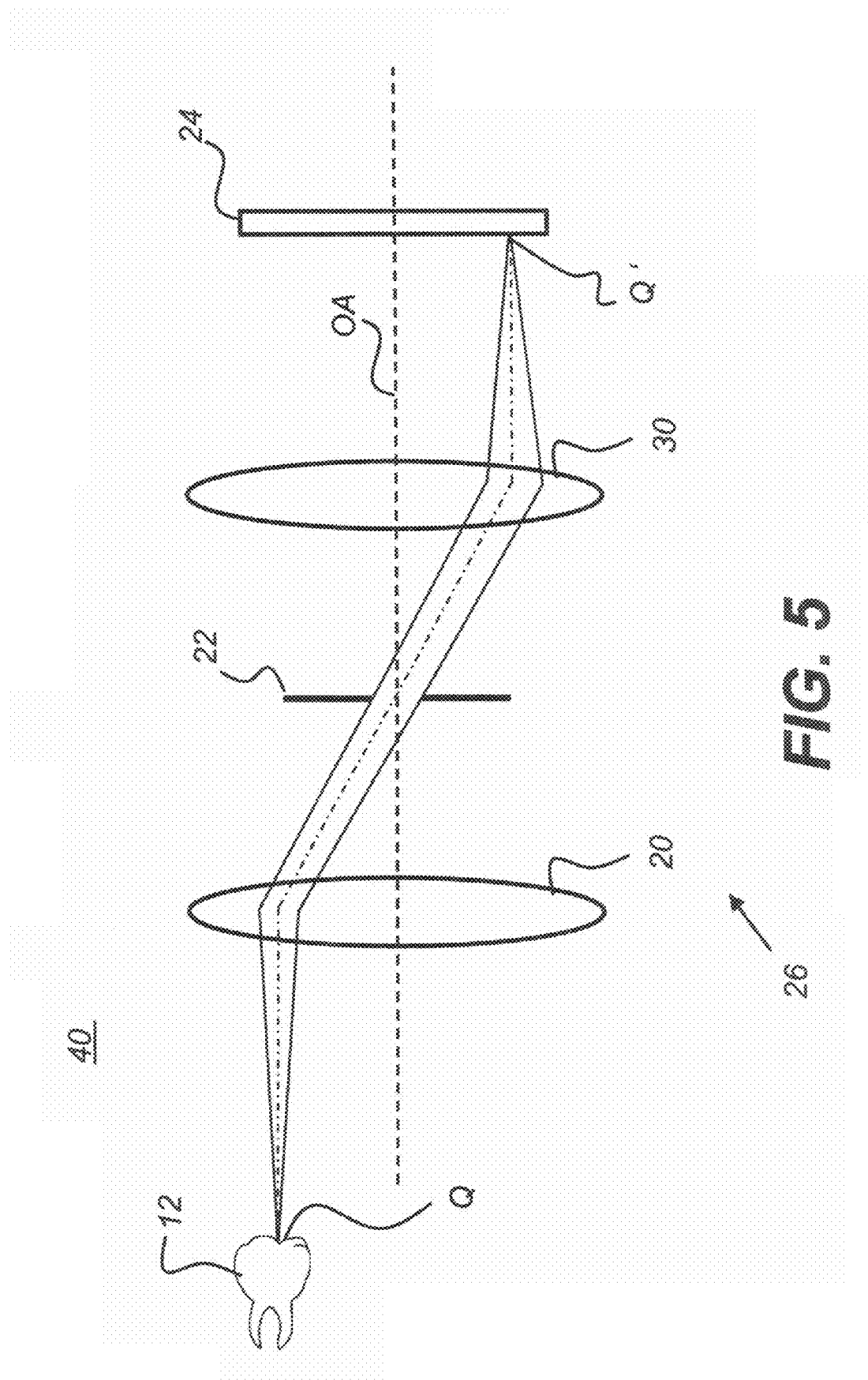
FIG. 5 is a schematic diagram that shows behavior and some basic components of a double telecentric imaging apparatus according to aspects of the present invention.

Referring to FIG. 5, there is shown a schematic diagram of a double telecentric imaging apparatus 40 used for dental imaging according to one embodiment of the present invention. A tooth 12 is shown in the object field. A narrow cone of rays centered about the chief rays is shown emanating from a point Q on the surface of tooth 12. A lens assembly 26 has at least lenses 20 and 30 and includes aperture 22 at the common focal point of lenses 20 and 30. On a detector array 24 that is energizable to form a pixellated image, such as a CMOS or CCD image detector array, object point Q is imaged to point Q', that is, to the pixel sensor corresponding to point Q'. As noted earlier, the position of Q' on detector array 24 does not change with any variation in focus of imaging apparatus 40. That is, due to double telecentric design, the pixel sensor at Q' senses the light received from point Q on tooth 12, regardless of the distance between the imaging apparatus and the tooth. In this way, because magnification is maintained (as described in (i), above), each point in the object field has a corresponding point position in the two-dimensional image that is formed in the image plane and this point position in the image plane is maintained for any focus adjustment. Detector array 24 can be monochrome or color. A compact arrangement for an intra-oral imaging device is provided in an embodiment with detector array 24 and lens assembly 26 aligned along an optical axis that extends in one direction as shown in FIG. 5, without turning mirrors or other devices that redirect the path of the optical axis.

Figure 6:
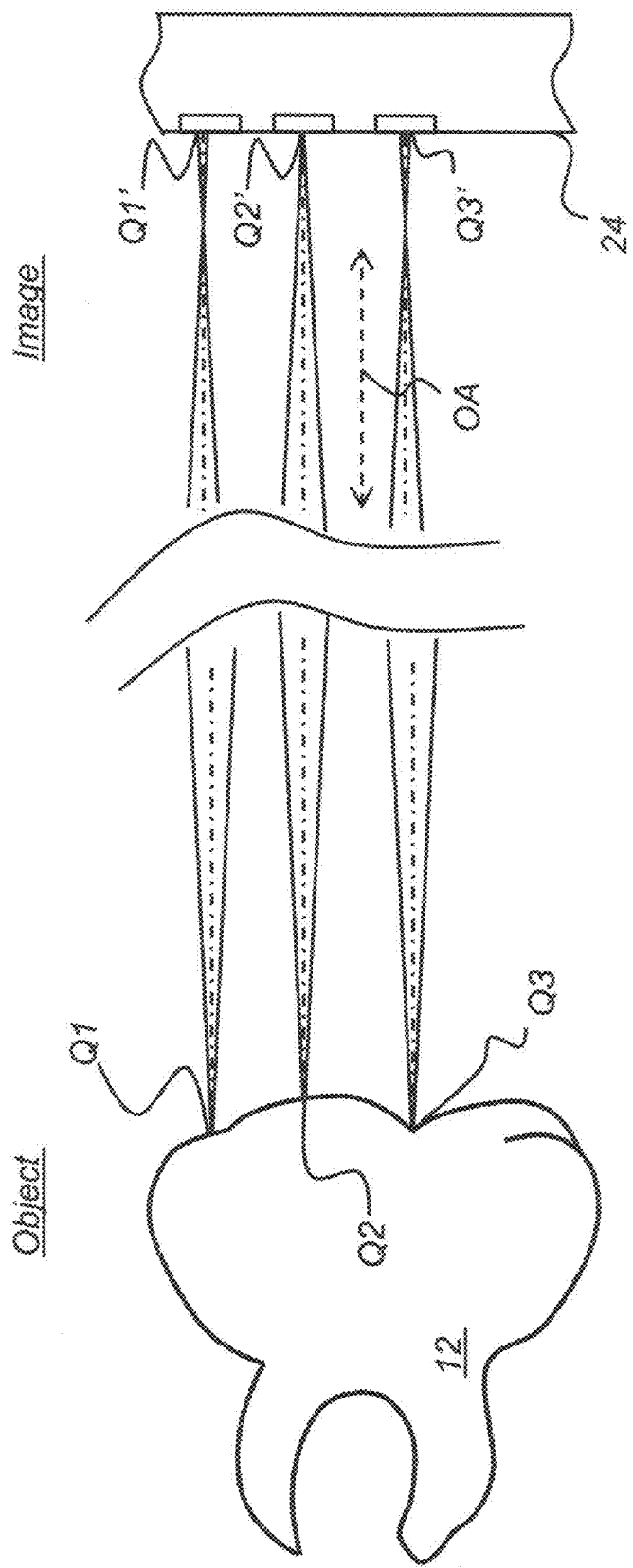
FIG. 6 is a schematic diagram showing how embodiments of the present invention employ the pattern of telecentric light in the object field and in the image field.

The apparatus and method of the present invention employ this principle of constant magnification, and consequent stationary pupil position, with variable focus to detect depth differences along the tooth surface. Since this depth information is available for every pixel on the tooth, the surface contour of the tooth can then be determined. The schematic diagram of FIG. 6 shows how telecentric light is used for depth measurement. Tooth 12 is in the object field at the left and presents an irregular surface for imaging, as shown. Light from each of surface points Q1, Q2, and Q3 is telecentric, so that the chief ray from each point is substantially in parallel with the optical axis OA. In the image field at the right, detector array 24 has a pixel Q1', Q2', and Q3' that corresponds to each surface point Q1, Q2, and Q3, respectively. This surface point-to-pixel correspondence is maintained at each focus position. As represented in FIG. 6, surface point Q2 is in focus relative to detector array 24, so that pixel Q2' receives focused light from that point on tooth 12. Surface points Q1 and Q3, meanwhile, are out of focus. As represented in FIG. 6, focus relates to the relative position of detector array 24 along the optical axis OA. For both points Q1 and Q3, focus is to the left of the current position of detector array 24. Thus, the light received at corresponding pixels Q1' and Q3' is past the focal point as shown in this figure.

With the image-space telecentric arrangement shown previously in FIG. 3, the only means available for focus adjustment was movement of detector array 24 along optical axis OA. However, with the double telecentric arrangement of imaging apparatus 40, as shown in FIG. 5, the focus distance can be changed in various ways: by moving detector array 24 along optical axis OA; or by moving the position of the lens assembly with respect to detector array 24; or by moving both the lens assembly and detector 24 as a unit, changing the distance to tooth 12, as described in more detail subsequently. 3-D depth information for each surface point can be obtained using the relative position of detector array 24 to the lens assembly, at focus for that point.

Figure 7:
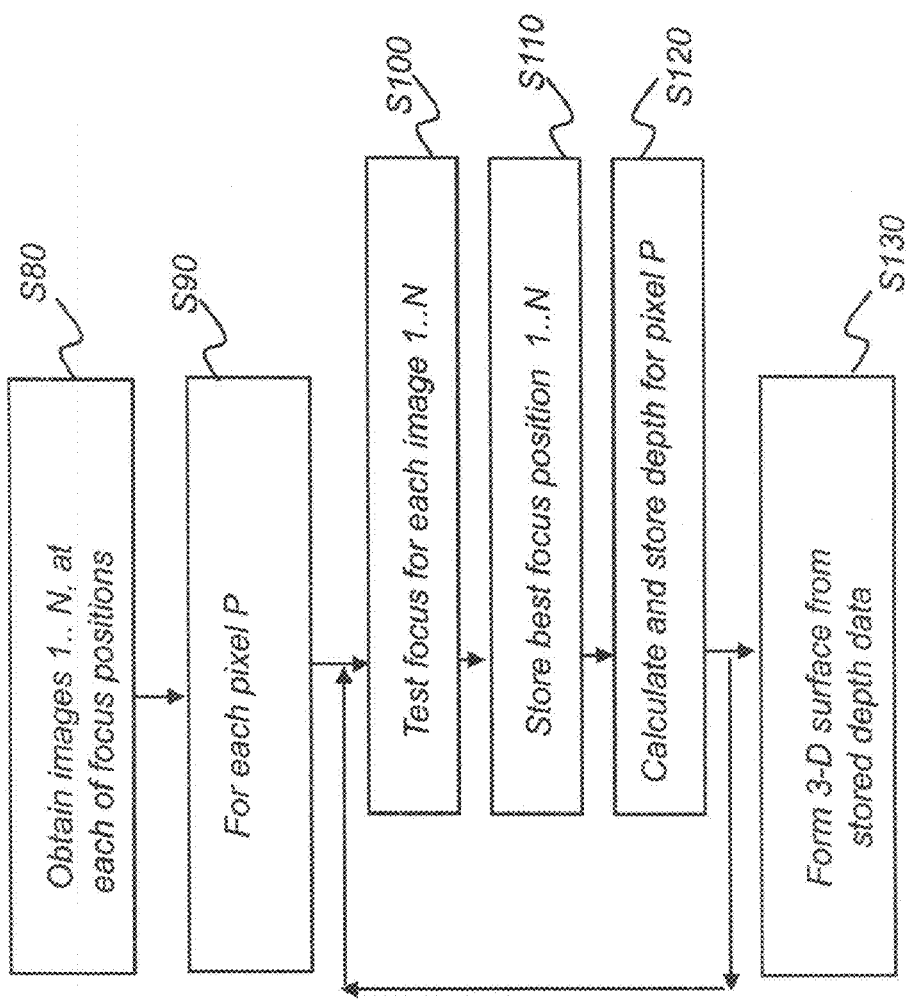
FIG. 7 is a logic flow diagram that shows the sequence for obtaining 3-D depth information from a double telecentric optical system according to aspects of the present invention.

The logic flow diagram of FIG. 7 shows the basic processing sequence that is used to obtain 3-D surface contour information from the depth data, using the optical component arrangement of FIG. 5 with added components for changing focus and processing data, as described in more detail subsequently. In an imaging step S80, a stepped-focus position sequence is employed. Multiple images 1 . . . N of the tooth are obtained, one for the image that is formed at each of N focus positions. In one embodiment, N is 100. This image capture is done automatically; the operator simply holds imaging apparatus 40 in position while an automated process performs a repeated sequence of capturing an image, then moving to the next focus position in sequence. In one embodiment, successive focus positions are spaced at even intervals 10 um apart.

Continuing with the logic flow of FIG. 7, a looping step S90 is then executed once multiple images have been obtained in step S80 and stored in an electronic memory. Looping step S90 controls execution of a focus assessment step S100 that determines which pixels in any of the N stored images are in focus. The corresponding focus position for each pixel is then stored in a focus store step S110. A depth calculation step S120 can then be performed using the stored focus position data, storing depth information for each pixel. Finally, a 3-D surface contour can be determined from the stored depth data. The 3-D contour data can then be stored in an electronic memory, displayed, or used in subsequent processing.

From an image processing perspective, obtaining surface contour information using the process of FIG. 7 with the double telecentric optics described herein with respect to FIG. 5 and the focus arrangement described with reference to FIG. 6 can be better understood by considering a single point in the scene, such as Q2 in FIG. 6. It is well known to those skilled in the art that a measure of focus for a region is the relative contrast. A measure of the contrast of a region, in turn, is the variance.

At the image pixel level, an out-of-focus condition can be considered as the result of a convolution of the image with a blur filter. A blur filter reduces the high frequency content of the image. As noted earlier, one aspect of a telecentric system is that there is no magnification of the image as the image plane is shifted. Consequently, the position of the point in the scene (Q2 in this example) has the same pixel location (Q2') in each image. As the focal plane is shifted, the window of neighboring pixels contains the same portion of the scene. By computing the variance of other pixels in the neighborhood of the pixel, and using this type of computation in each image in the focus sequence, a measure of the contrast of the pixel at every focus position, that is, image plane position, can be obtained. The focus position that yields the largest variance value indicates where the single point selected (Q2) provides a pixel (Q2') that is in best focus. Using the well known thin lens equation and other camera parameters, an estimate of the depth of the pixel can be readily estimated using this focus information. This procedure can be iteratively performed for every pixel, resulting in a depth estimate for every pixel.

Figure 8:
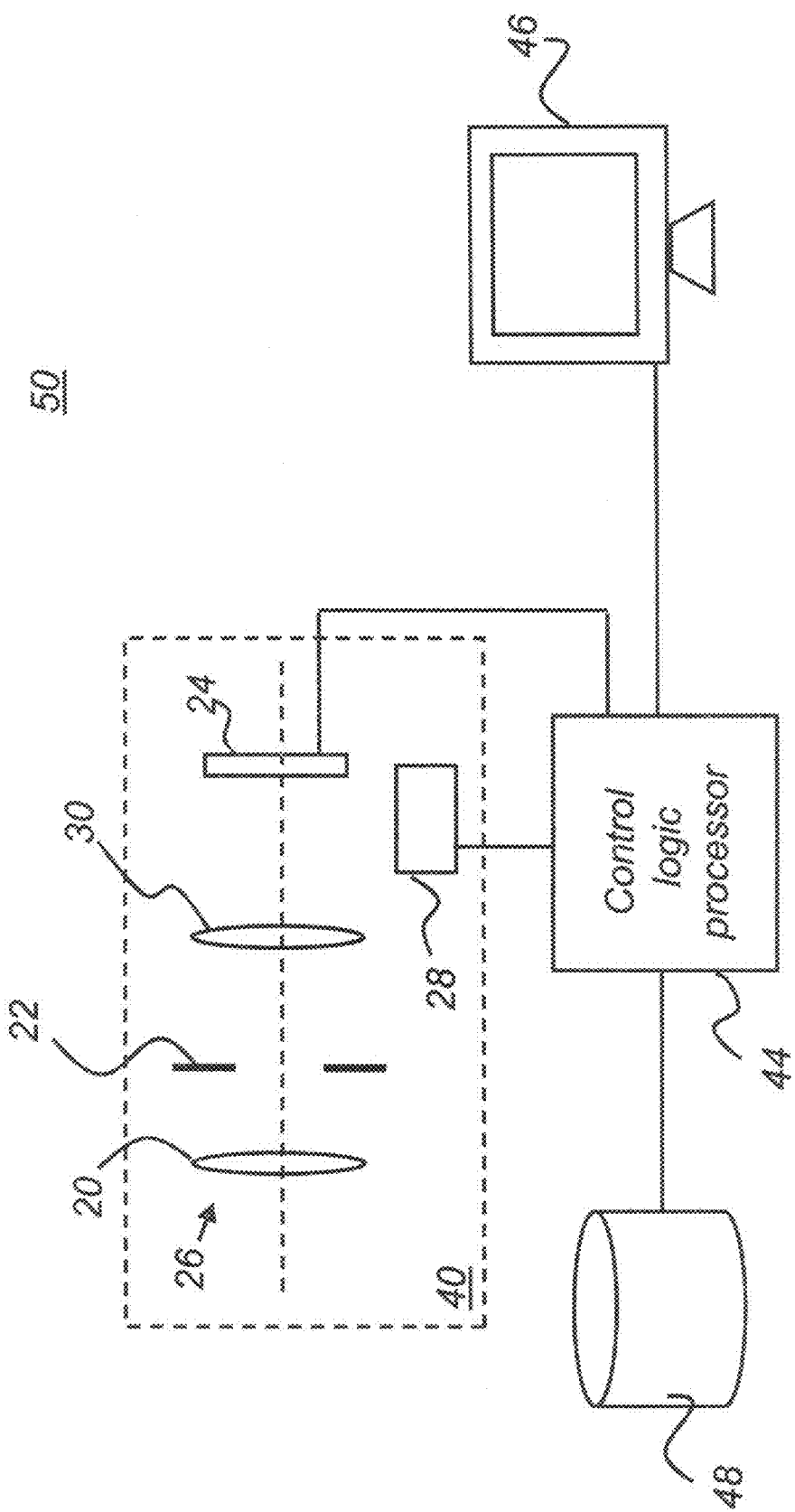
FIG. 8 is a block diagram showing components of an intraoral imaging system according to one embodiment.

The block diagram of FIG. 8 shows a 3-D imaging system 50 that provides 3-D image data using imaging apparatus 40 with the stepped-focus position sequence described with reference to FIGS. 6 and 7. A control logic processor 44 provides the signals that coordinate focus adjustment and performs the needed calculations for providing depth information. For focus adjustment to each of a sequence of focus positions, control logic processor 44 is in control signal communication with an actuator 28 that provides a focus adjustment mechanism. Control signals, initiated from control logic processor 44, cause actuator 28 movement to each position in the sequence.

For obtaining and storing image data for each focus position in the sequence, control logic processor 44 is in image data communication with detector array 24. Image data communication can be by means of a parallel or serial data connection, for example. In response to stored instructions, control logic processor 44 stores the image data for each focus position in a computer-accessible electronic memory 48, which may be external to control logic processor 44. Control logic processor 44 performs the image processing that is needed for providing surface information or, alternately, communicates with an external processor for performing this processing. A combination of processors internal to an intra-oral imaging apparatus or externally provided may perform logic processing functions. A display 46 is provided as part of imaging system 50, providing a displayed image following the image capture sequence and 3-D surface data processing. Advantageously, a full-color image is obtained and can be displayed with the surface information that is computed.

Figure 9:
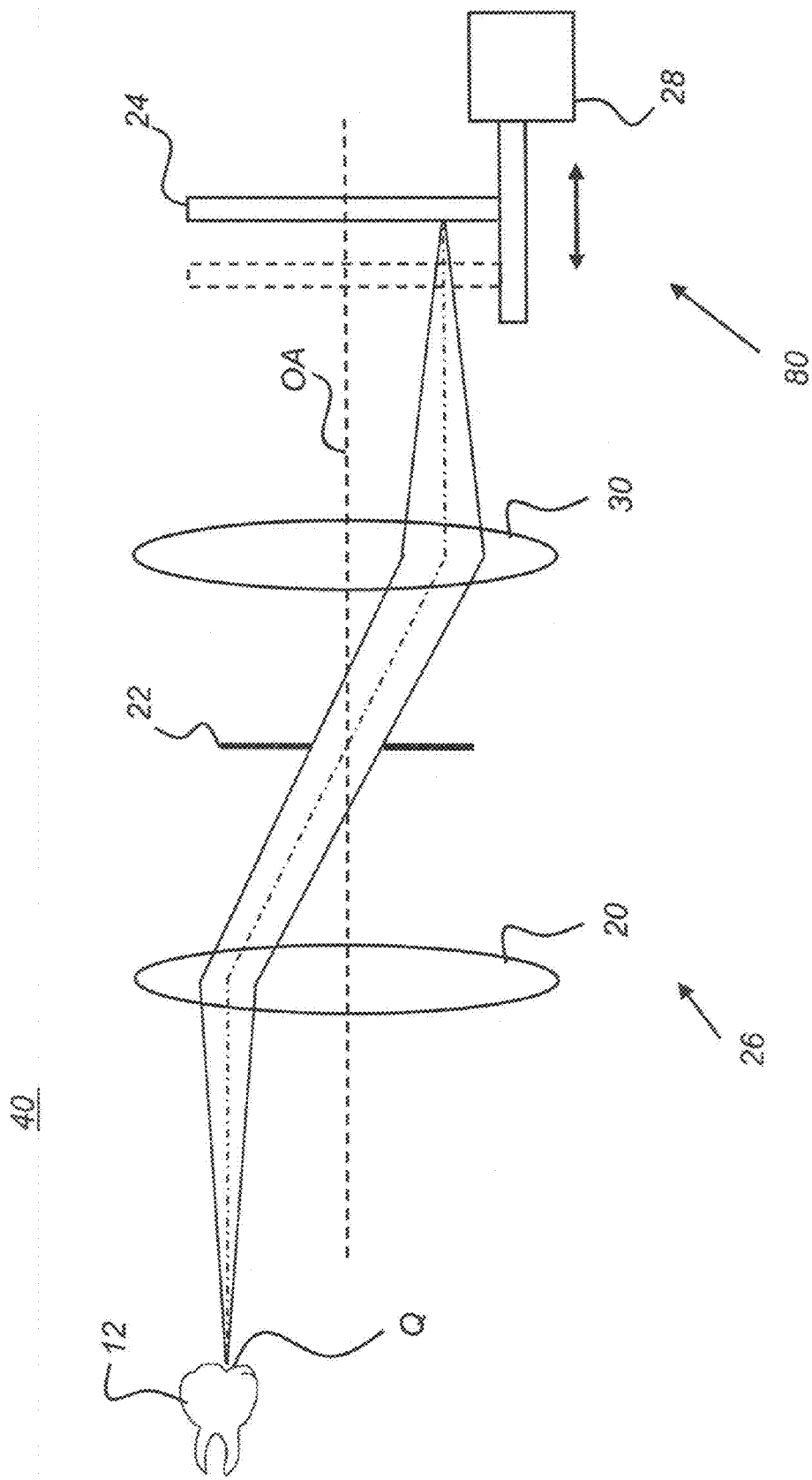
FIG. 9 is a schematic diagram that shows using detector movement for changing focus to enable depth detection.
Figure 10:
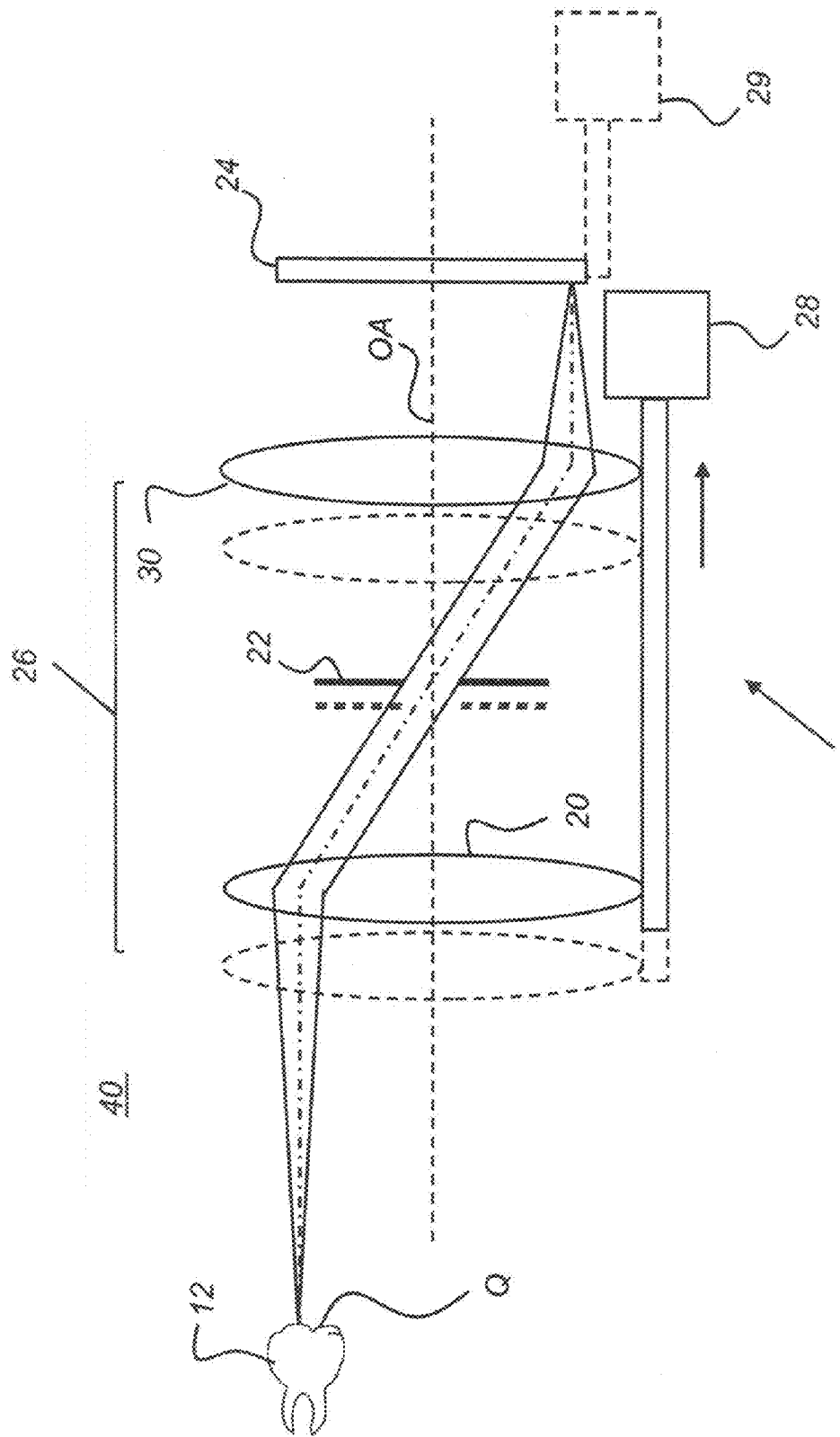
FIG. 10 is a schematic diagram that shows using lens movement for changing focus to enable depth detection.

Focus positions can be changed by adjusting the relative distance on the object side, between lens assembly 26 and tooth 12 or, on the image side, between lens assembly 26 and detector array 24. This focus adjustment can be done in a number of ways. By way of example, the schematic diagrams of FIGS. 9 and 10 show two different ways in which multiple focus positions can be achieved by a focus adjustment mechanism 80 using imaging apparatus 40 of the present invention. FIG. 9 shows an embodiment of imaging apparatus 40 that has actuator 28 operatively connected with detector array 24 and actuable to sequentially adjust the relative position of focus to detector array 24 in image space of the double telecentric optical system to each of a number of focus positions. In the embodiment shown, actuator 28 moves detector array 24 in increments along optical axis OA, relative to lens assembly 26, thereby changing focus from one position to the next.

FIG. 10 shows an alternate embodiment of imaging apparatus 40 that has actuator 28 of focus adjustment mechanism 80 operatively connected with lens assembly 26 to move the associated optical components along optical axis OA, thereby changing focus from one position to the next. In this embodiment, detector array 24 does not move along the optical axis OA.

A third technique for achieving multiple focus positions is to move both detector array 24 and lens assembly 26 along optical axis OA as a single unit, toward or away from tooth 12 or other dental feature. For this technique, detector array 24 and lens assembly 26 are fixed in position along the optical axis relative to each other, but are moved together by one or more actuators 28 of focus adjustment mechanism 80, to each of a number of focus positions. FIG. 10 shows one embodiment, with an optional actuator 29, shown in dashed outline, disposed to shift detector array 24 in conjunction with movement of lens assembly 26. A single actuator is used in an alternate embodiment.

Actuator 28 of focus adjustment mechanism 80 can be any of a number of types of devices that are actuable to allow controllable movement in sufficiently small increments. In one embodiment, actuator 28 is a linear piezoelectric actuator. A stepper motor or other type of rotating motor with a leadscrew, belt, or other suitable mechanism capable of providing the needed spatial resolution could alternately be used.

Figure 11:
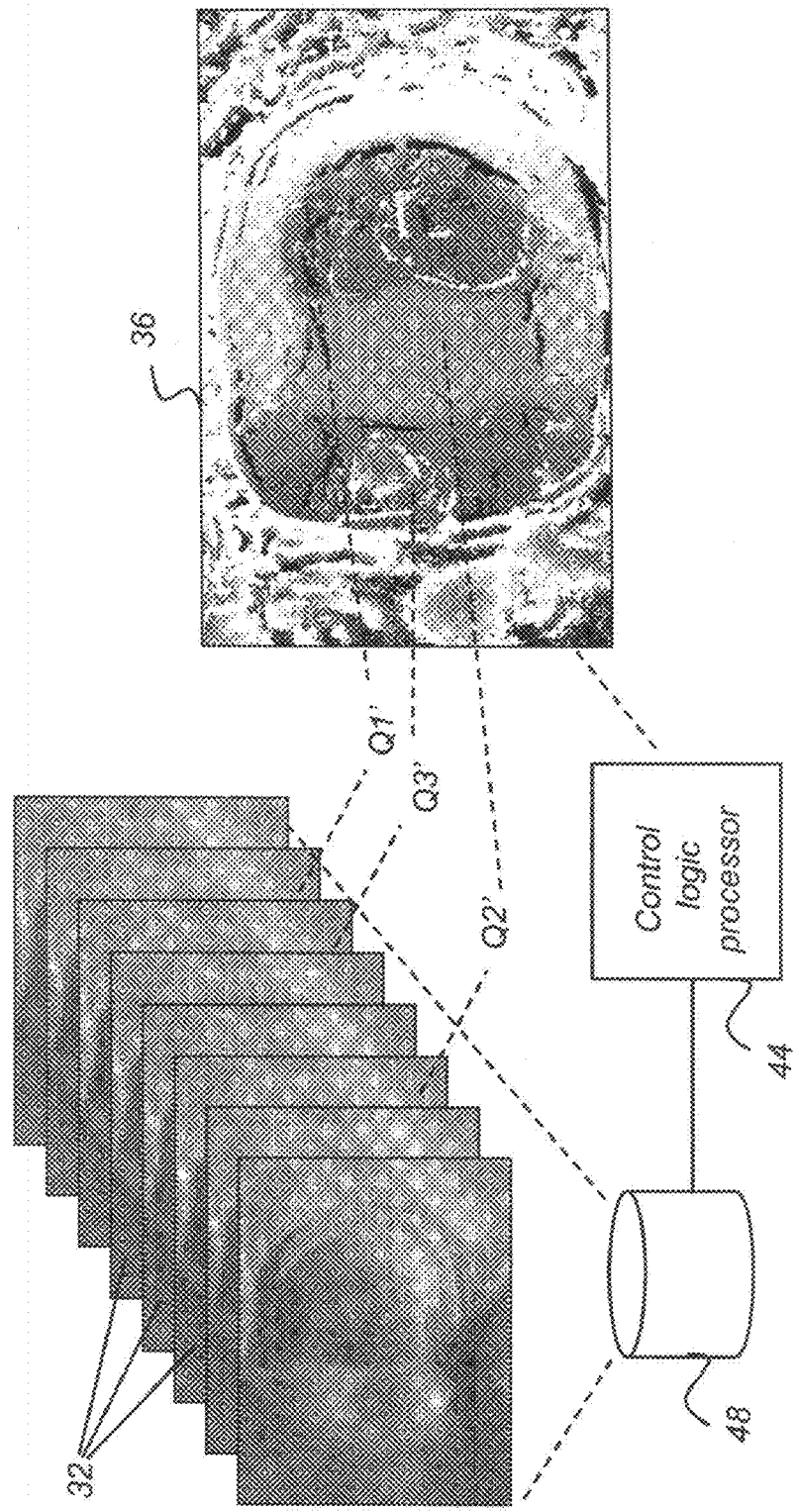
FIG. 11 is a diagram showing the use of multiple images, each at a different focus, for reconstructing an image showing surface contour.

FIG. 11 is a diagram showing how a 3-D surface image is reconstructed from multiple images obtained by imaging apparatus 40. At each focus position, an image 32 is captured by detector array 24 and stored in an electronic memory accessible to control logic processor 44, as described earlier with reference to FIG. 8. Control logic processor 44 executes the logic of depth calculation step S120 and surface forming step S130 (FIG. 7) that analyzes focus information to calculate the depth information that is associated with each pixel. The result is a 3-D contour image 36 that is reconstructed from the pixel depth calculations and can be displayed, transmitted over a network, or stored. As shown in the example of FIG. 11, each of pixels Q1', Q2', and Q3' represents a point on the tooth that is at a different depth and is thus obtained from a different captured image 32.

Figure 12:
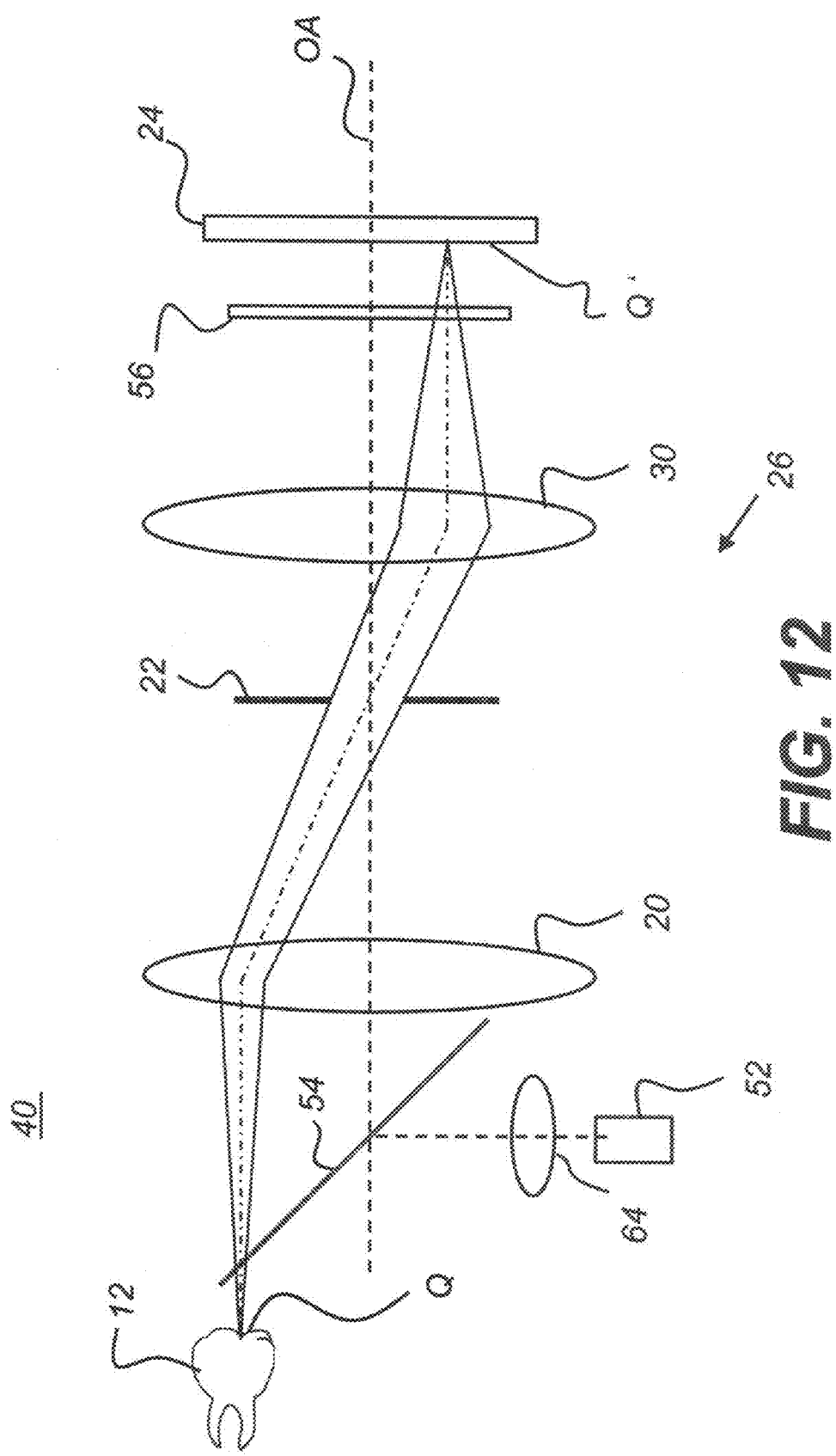
FIG. 12 is a schematic diagram of an imaging apparatus using polarized illumination for depth defocus imaging.

Illumination for the imaging apparatus can be provided by a separate light source, including an auxiliary attachment to the imaging apparatus, with the path of the illumination either through or external to the double telecentric optical system. Alternately, as shown in the embodiment of FIG. 12, a uniform field of illumination can be provided by a light source 52 that is internal to imaging apparatus 40 or that is directed into imaging apparatus 40 using an optical fiber, for example. Unlike confocal imaging designs, the illumination path does not need to extend through the double telecentric optics. Projection optics 64 condition the illumination that is provided to provide the illumination as a uniform beam over the object field. In the FIG. 12 embodiment, light source 52, such as a light-emitting diode (LED) or other solid-state light source, directs light toward tooth 12 using a beamsplitter 54. This enables at least some of the light from light source 52 to illuminate the tooth surface and to be reflected and used for depth detection. A polychromatic light source, also termed a white light source, is used in one embodiment and provides a color image of the tooth; however, an arrangement with one or more color light sources could be used.

Polarized light can alternately be used as the illumination source. Polarized light can be advantaged for reducing specular reflection, for example. Referring again to the schematic of FIG. 12, beamsplitter 54 can be a polarization beamsplitter that reflects light of one polarization toward tooth 12 and transmits reflected light of the orthogonal polarization for depth detection at detector array 24. Other types of polarizer could alternately be used. An optional analyzer 56 may also be provided in the path of received light.

For many teeth and other dental objects, there is sufficient surface texture or roughness for depth imaging using the sequence of FIG. 7. FIGS. 13A-13C show an example tooth 12 at FIG. 13A for which depth imaging is successful. A graph 70 at FIG. 13C shows raw measurement data, prior to noise filtering, that is clearly usable to obtain a profile of the tooth surface. An image 72 at FIG. 13B shows a portion of a reconstructed surface that is obtained using this data.

The alternate example of FIGS. 14A-14B, however, show a portion of the surface of an artificial tooth 12 that is exceptionally smooth and more difficult to obtain surface data from. An image 74 shows the results for surface reconstruction with the focus technique and sequence of FIG. 7. As image 74 shows, surface information is relatively unclear for this example.

As the FIGS. 14A-14B example shows, using contrast and variance data for obtaining surface contour information can have some limitations. If an area is devoid of features and very smooth, for example, it can be difficult to differentiate the measured contrast or variance values from noise. Considering again the blur filter processing model introduced earlier, it can be observed that blur has no effect for an image that has no perceptible high-frequency content.

To overcome this limitation and to allow contour data to be obtained from a smooth tooth surface such as that shown in FIGS. 14A-14B, measures that help to enhance small variations in the tooth surface can be used, provided that the topography of the scene is not corrupted. Such measures can include dusting the scene by applying a fine particulate, for example.

Figure 15B:
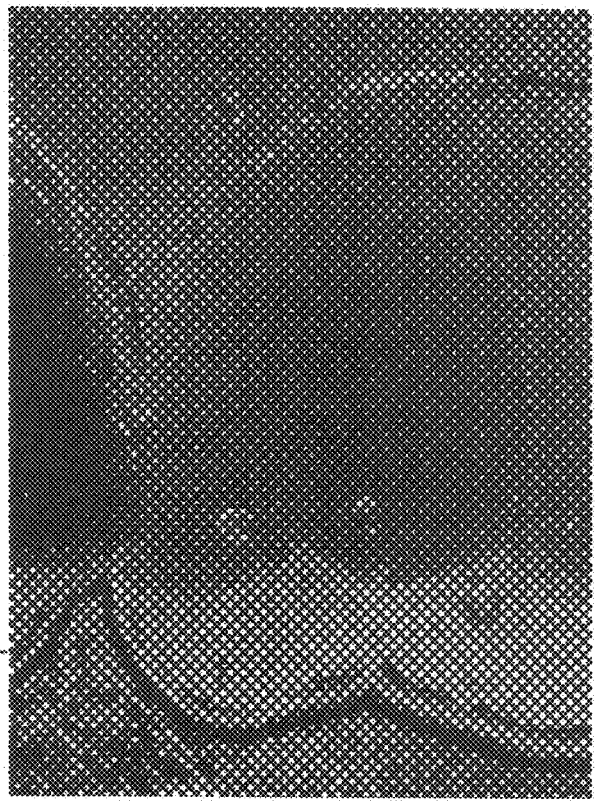
FIGS. 15A and 15B show the use of a projected pattern in conjunction with depth detection for the smooth surface shown in FIGS. 14A and 14B.
Figure 15A:
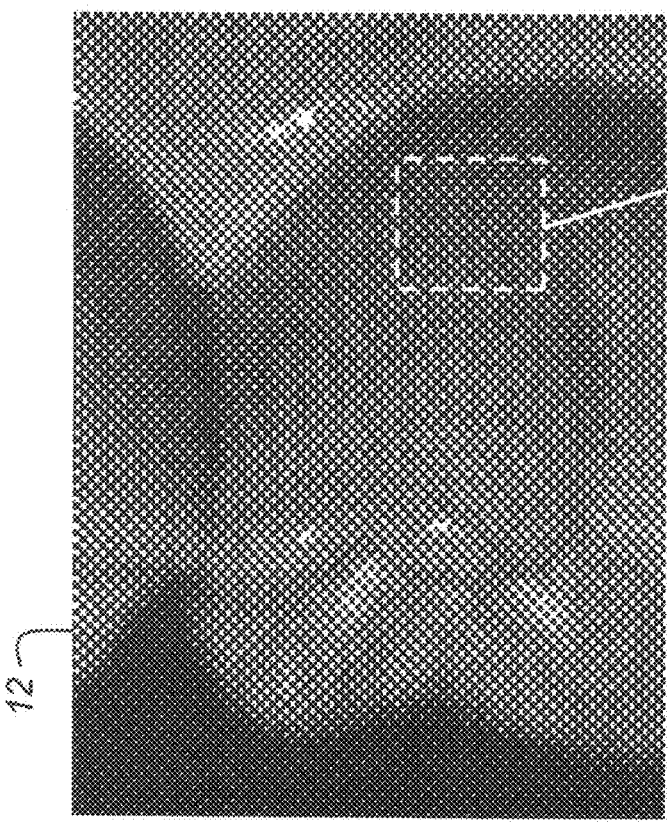

Another method for enhancing the surface contour for smooth surface conditions such as those of FIGS. 14A-14B is projecting a texture pattern onto the scene. Additional information can then be obtained by using focus information relative to the projected pattern. Referring to FIGS. 15A-15B, a pattern 78 is projected onto tooth 12 during the sequence of FIG. 7. Focus information is computed from the projected pattern, yielding the improved reconstructed surface image 74.

As FIGS. 15A-15B show, patterned illumination, when used in combination with depth defocus, can obtain an even higher degree of accuracy for tooth surface imaging. In the context of the present disclosure, the term "pattern illumination" or "patterned illumination" is used to describe the type of structured illumination that is used for fringe projection imaging or "contour" imaging. The pattern itself can include, as pattern features, multiple lines, dots, checkerboard, or other geometric shapes that are distributed over the area that is illuminated and that have a predetermined spatial frequency, recurring at a given period. A two-dimensional pattern, such as a checkerboard pattern, offers advantages for providing surface contour information over projected parallel lines. The illumination pattern gives texture to the object surface and thus helps to extract the contrast map for higher spatial resolution. The illumination pattern is tuned to maximize depth accuracy and resolution. This method is especially effective for objects having a relatively smooth surface and can be used in conjunction with a coating or powder, for example.

Figure 16:
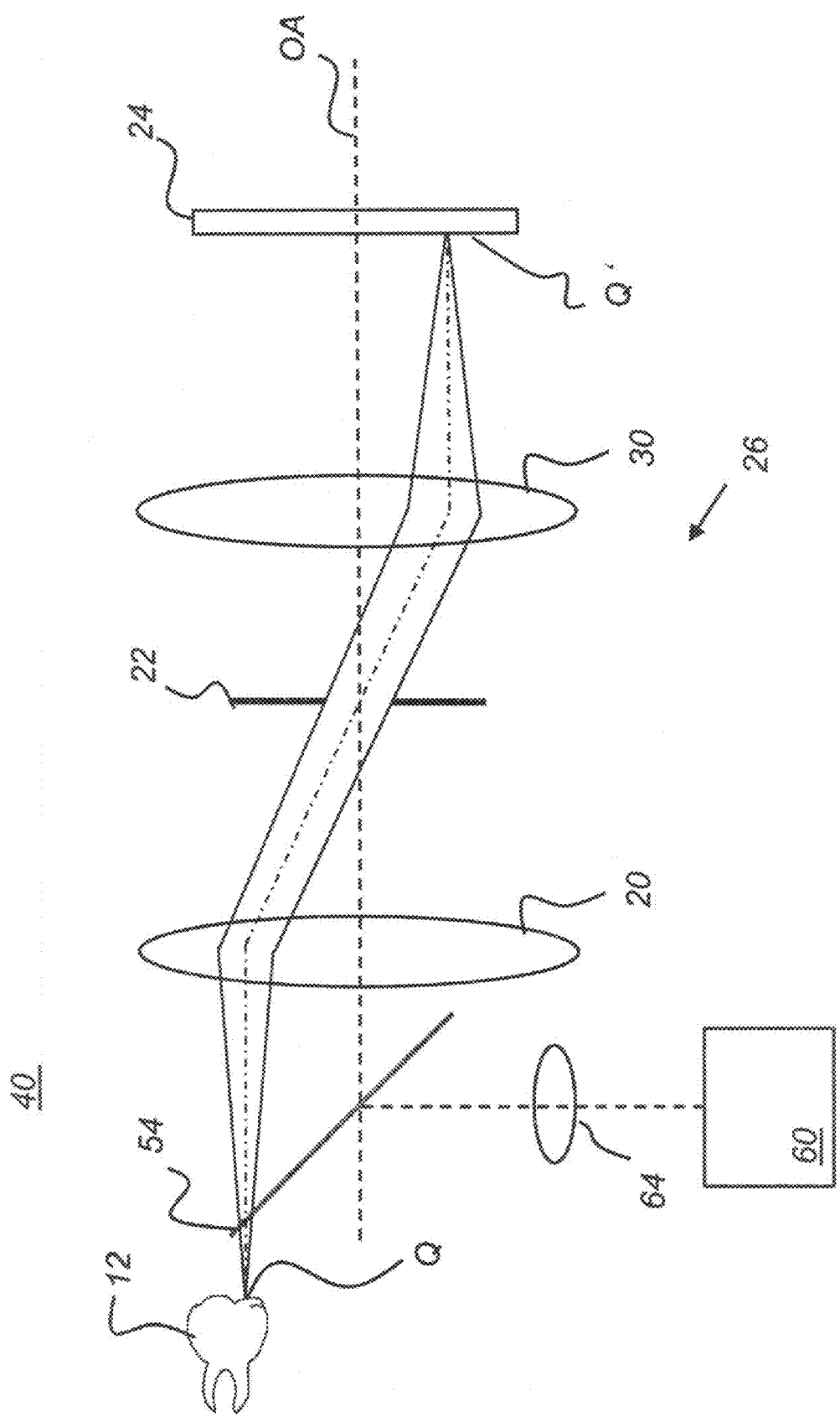
FIG. 16 is a schematic diagram of an imaging apparatus that combines aspects of projection fringe imaging with depth defocus imaging.

Referring to FIG. 16, there is shown a schematic diagram of imaging apparatus 40 that includes a pattern generator 60, energizable to direct a patterned illumination onto the tooth 12 surface. Pattern generator 60 includes a solid-state light source in one embodiment and is in image data communication with control logic processor 44 for forming one or more different types of patterns on the tooth. Additional polarization components could be employed to improve pattern image projection performance, as noted in commonly assigned patent application U.S. Ser. No. 12/424,562 filed on 16 Apr. 2009 entitled "DENTAL SURFACE IMAGING USING POLARIZED FRINGE PROJECTION" to Liang. This can include polarization beamsplitter 54 and analyzer 56 for the patterned illumination, as shown previously in FIG. 12, for example. When used in combination with depth imaging, a structured projection pattern does not require phase shifting, as with conventional projection fringe imaging. This is because the focus detection algorithms operate on an image that includes the pattern itself.

In the case of projecting a pattern onto the scene, the geometry of the projected texture pattern needs to be compatible with the window dimensions used to compute variance. A reasonable rule of thumb is that a full cycle of the projected texture should be contained within the window. Otherwise, the statistics used to estimate the variance can have spatial correlations that skew the results.

Even when a particulate is applied or a pattern projected, however, the resulting images may still not contain sufficient information to estimate the depth or extent of surface features with any degree of confidence. There may be, for example, steep edges or a point in the scene that lies outside the focal range of the imaging system, for example, a point far exceeding the expected distances of interest. If this occurs, it can be useful to identify and flag pixels in these areas. One method of identifying these pixels is to compare the variance around the pixel of interest at the selected image plane and the variance of that pixel at the maximum extents of the positions of the image plane. If the maximum difference of the variance is less than some predetermined threshold, then the pixel is identified as indeterminate. In one embodiment, a threshold of 10 variance units was derived empirically and provided reasonable identification of pixels having unreliable depth estimates.

It is noted that the combination of a double telecentric optical system with an adjustable focus mechanism enables depth detection from focus information, as used in embodiments of the present invention. Unlike other apparatus such as confocal depth detection or fringe projection devices, imaging apparatus 40 of the present invention obtains and uses focus information from successive 2-D images of the tooth rather than from mapped points or from a projected fringe pattern. An advantage of this arrangement over other contour imaging approaches is that contour information, once obtained, can be correlated more readily with other image content, since the contour information can be computed for each pixel of the image. Color or monochrome images can be obtained.

The invention has been described in detail with particular reference to a presently preferred embodiment, but it will be understood that variations and modifications can be effected within the spirit and scope of the invention. For example, the invention can be used to obtain depth information from teeth as well as other intra-oral structures. Control logic processor 44, described with reference to FIG. 8, can be any of a number of types of control logic device that are responsive to stored instructions, such as a microprocessor, a dedicated processor, a computer or computer workstation, or one or more networked computers, workstations, or host processors.

The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. Lens
12. Tooth
20. Lens
22. Stop
24. Detector array
26. Lens assembly
28, 29. Actuator
30. Lens
32. Image
36. 3-D contour image
40. Imaging apparatus
44. Control logic processor
46. Display
48. Memory
50. 3-D imaging system 52. Light source
54. Beamsplitter
56. Analyzer
60. Fringe pattern generator
64. Projection optics
70. Graph
72. Image
74. Image
78. Pattern
80. Focus adjustment mechanism
A, B, C. Object
A', B', C'. Image
F. Focal point
OA. Optical axis
Q. Point
Q' Pixel
S80. Imaging step
S90. Looping step
S100. Focus assessment step
S110. Focus store step
S120. Depth calculation step
S130. Surface forming step

What is claimed is:

1. An apparatus for obtaining 3-D surface contour image data of a tooth, comprising:
   a double telecentric optical system configured to form an image of a surface of the tooth onto an image detector array;
   a focus adjustment mechanism actuable to adjust a position of either or both the double telecentric optical system and the image detector array along an optical axis to each of a sequence of focus positions; and
   a control logic processor in control signal communication with the focus adjustment mechanism to adjust focus position, and in image data communication with the image detector array for receiving image data obtained by the image detector array and with a memory for storing the received image data corresponding to each of the sequence of focus positions, wherein the control logic processor is configured to determine, for each of a plurality of pixels in the received image data, a corresponding depth value according to pixel contrast,
   wherein the control logic processor is further responsive to stored instructions for computing the 3-D surface contour image data from the stored image data.

2. The apparatus of claim 1 wherein the detector array is a CMOS or CCD detector.

3. The apparatus of claim 1 wherein the focus adjustment mechanism comprises a piezoelectric actuator.

4. The apparatus of claim 1 wherein the control logic processor is further responsive to stored instructions that detect the relative focus of each of a plurality of pixels in the stored image data.

5. The apparatus of claim 1 further comprising a polychromatic light source for directing illumination toward the tooth.

6. The apparatus of claim 5 wherein the light source has an illumination path that is external to the double telecentric optical system.

7. The apparatus of claim 5 further comprising a polarizer in the path of the illumination.

8. The apparatus of claim 1 further comprising a pattern generator that is energizable to direct a pattern of illumination onto the surface of the tooth.

9. The apparatus of claim 1 wherein the focus adjustment mechanism is actuable to move elements of the double telecentric optical system to positions along the optical axis, but does not move the image detector array.

10. The apparatus of claim 1 wherein the focus adjustment mechanism is actuable to move the detector array to positions along the optical axis, but lens elements of the double telecentric optical system remain stationary along the optical axis.

11. A method for obtaining 3-D surface contour image data of a tooth, comprising:
    disposing, in the image plane of a double telecentric optical system, an image detector array energizable to form an image;
    adjusting the position of either or both the double telecentric optical system and the image detector array along an optical axis to each of a sequence of focus positions;
    obtaining image data from the detector array at each focus position in the sequence and storing the image data in an electronic memory;
    calculating the focus of each of a plurality of pixels in the obtained image data and determining, for each of the pixels, a corresponding depth value according to pixel contrast;
    combining a plurality of the determined depth values to form the 3-D surface contour image; and
    displaying the 3-D surface contour image.

12. The method of claim 11 further comprising directing a patterned illumination toward the tooth.

13. The method of claim 12 wherein directing a pattern of illumination toward the tooth comprises energizing a solid state light source.

14. The method of claim 11 wherein adjusting the position of either or both the double telecentric optical system and the image detector array comprises energizing a piezoelectric actuator.

15. The method of claim 11 wherein adjusting the position of either or both the double telecentric optical system and the image detector array comprises energizing an actuator to move the detector array.

16. An apparatus for obtaining 3-D surface contour image data of a tooth, comprising:
    a pattern generator energizable to direct an illumination pattern on a surface of the tooth;
    a detector array energizable to form an image;
    a double telecentric optical system disposed to direct light reflected from the surface of the tooth to the detector array;
    a focus adjustment mechanism actuable to adjust the position of either or both the double telecentric optical system and the image detector array along an optical axis to each of a sequence of focus positions; and
    a control logic processor in image data communication with the detector array and with the pattern generator and responsive to instructions for storing the image data for each of the sequence of focus positions in a memory, for calculating a focus of each of a plurality of pixels in the stored image data, for determining, for each of the pixels, a corresponding depth value according to pixel contrast, and for computing the 3-D surface contour image data from the stored image data.

17. The apparatus of claim 16 wherein the detector array is a CMOS or CCD detector.

18. The apparatus of claim 16 wherein the focus adjustment mechanism moves elements of the double telecentric optical system to positions along an optical axis.

19. The apparatus of claim 16 wherein the focus adjustment mechanism moves the detector array to positions along an optical axis.

20. The apparatus of claim 16 wherein the illumination pattern is a checkerboard pattern.

* * * * *

UNITED STATES PATENT AND TRADEMARK OFFICE
CERTIFICATE OF CORRECTION

| | | |
|---|---|---|
| PATENT NO. | : 8,134,719 B2 | Page 1 of 1 |
| APPLICATION NO. | : 12/727671 | |
| DATED | : March 13, 2012 | |
| INVENTOR(S) | : Liang et al. | |

It is certified that error appears in the above-identified patent and that said Letters Patent is hereby corrected as shown below:

The Title page, Item no. (56), Please delete "0,008,139 A1" and insert --2002/0008139 A1--.

Signed and Sealed this
Tenth Day of July, 2012

David J. Kappos
*Director of the United States Patent and Trademark Office*